United States Patent
Wada (10) Patent No.: US 10,206,659 B2
(45) Date of Patent: Feb. 19, 2019

(54) UNIMORPH-TYPE ULTRASOUND PROBE AND METHOD FOR MANUFACTURING THE SAME

(71) Applicant: FUJIFILM Corporation, Tokyo (JP)

(72) Inventor: Takatsugu Wada, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 732 days.

(21) Appl. No.: 14/750,681

(22) Filed: Jun. 25, 2015

(65) Prior Publication Data

US 2015/0289843 A1 Oct. 15, 2015

Related U.S. Application Data

(63) Continuation of application No. PCT/JP2013/081763, filed on Nov. 26, 2013.

(30) Foreign Application Priority Data

Dec. 26, 2012 (JP) .................. 2012-282778

(51) Int. Cl.
*A61B 8/14* (2006.01)
*A61B 8/00* (2006.01)
*B06B 1/06* (2006.01)

(52) U.S. Cl.
CPC .......... *A61B 8/4494* (2013.01); *A61B 8/4461* (2013.01); *B06B 1/0622* (2013.01);
(Continued)

(58) Field of Classification Search
CPC ........ A61B 8/00; A61B 8/4461; A61B 8/4494
See application file for complete search history.

(56) References Cited

U.S. PATENT DOCUMENTS 6,307,302 B1 * 10/2001 Toda ................ B06B 1/067
310/327
6,584,660 B1 * 7/2003 Shimogawa ......... B41J 2/14233
219/121.69
(Continued)

FOREIGN PATENT DOCUMENTS

JP  2-261438 A  10/1990
JP  4043790 B2  2/2008
(Continued)

OTHER PUBLICATIONS

Chinese Office Action dated Jun. 22, 2016 in corresponding Chinese PatentApplication No. 201380068066.8 with English Translation.
(Continued)

*Primary Examiner* — Joel F Brutus
(74) *Attorney, Agent, or Firm* — Birch, Stewart, Kolasch & Birch, LLP (57) ABSTRACT

A unimorph-type ultrasound probe includes a substrate in which a plurality of openings each having a predetermined shape is formed, a plurality of vibration plates formed on the substrate so as to close one end of each of the plurality of openings, a plurality of piezoelectric element portions which is formed on a surface of the plurality of vibration plates and each has a piezoelectric substance layer and a pair of electrode layers formed on both surfaces of the piezoelectric substance layer, and a covering layer which is disposed on a surface of the substrate such that the plurality of piezoelectric element portions is embedded in the covering layer, and is formed of an organic resin having an acoustic impedance of $1.5 \times 10^6$ kg/m$^2$ s to $4 \times 10^6$ kg/m$^2$ s and a Shore A hardness of equal to or less than 75.

19 Claims, 7 Drawing Sheets

(52) U.S. Cl.
CPC ............. *A61B 8/00* (2013.01); *A61B 2562/12* (2013.01); *H04R 2217/00* (2013.01)

(56) References Cited

U.S. PATENT DOCUMENTS

| | | | |
|---|---|---|---|
| 2002/0105250 A1 | 8/2002 | Klee et al. | |
| 2003/0102777 A1* | 6/2003 | Kuniyasu | B06B 1/0629 310/334 |
| 2006/0238067 A1 | 10/2006 | Dausch | |
| 2009/0322181 A1* | 12/2009 | Machida | B06B 1/0292 310/300 |
| 2011/0013256 A1* | 1/2011 | Uchiyama | B81B 3/0008 359/290 |
| 2011/0284995 A1* | 11/2011 | Kuypers | B81B 7/02 257/622 |
| 2012/0306316 A1* | 12/2012 | Nakamura | H01L 41/0973 310/322 |

FOREIGN PATENT DOCUMENTS

| | | |
|---|---|---|
| JP | 2008-535643 A | 9/2008 |
| JP | 2012-253405 A | 12/2012 |

OTHER PUBLICATIONS

International Search Report for PCT/JP2013/081763, dated Jan. 7, 2014.
Japanese Office Action, dated Mar. 15, 2016, for corresponding Japanese Application No. 2014-554259, with a partial English translation.
English Translation of International Search Report for PCT/JP2013/081763, dated Jan. 7, 2014.

\* cited by examiner

UNIMORPH-TYPE ULTRASOUND PROBE AND METHOD FOR MANUFACTURING THE SAME

CROSS-REFERENCE TO RELATED APPLICATIONS

This application is a Continuation of PCT International Application No. PCT/JP2013/081763 filed on Nov. 26, 2013, which claims priority under 35 U.S.C. § 119(a) to Japanese Application No. 2012-282778 filed on Dec. 26, 2012. Each of the above application(s) is hereby expressly incorporated by reference, in its entirety, into the present application.

BACKGROUND OF THE INVENTION

The present invention relates to a unimorph-type ultrasound probe and a method for manufacturing the same. Particularly, the present invention relates to a unimorph-type probe, which is prepared by a micromachining technique, and a method for manufacturing the same.

Conventionally, in the medical field, an ultrasound diagnostic apparatus using ultrasound images has been put to practical use. Generally, in this type of ultrasound diagnostic apparatus, an ultrasonic beam is transmitted toward the inside of a subject from an ultrasound probe, ultrasonic echo from the subject is received by the ultrasound probe, and the received signal is electrically processed, thereby generating an ultrasound image.

As the ultrasound probe, a transducer using a bulk piezoelectric substance has been used. However, in recent years, for example, as disclosed in JP 4043790 B and JP 2008-535643 A, a unimorph-type probe prepared by a micromachining technique has drawn attention because a micro-sized array transducer can be easily manufactured.

The unimorph-type probe is also referred to as a so-called pMUT (Piezoelectric Micromachined Ultrasound Transducer) and has a piezoelectric element which is formed by laminating a lower electrode layer, a piezoelectric substance layer, and an upper electrode layer in this order on a vibration plate formed by partially machining a substrate formed of silicon or the like.

In order to generate a high-accuracy ultrasound image by applying the ultrasound probe to ultrasound diagnosis, the piezoelectric element needs to be driven at a high speed in a MHz band. However, if the piezoelectric element is driven at such a high speed, stress that is exerted between the respective layers, which are laminated on each other and come into close contact with each other, becomes significant. Furthermore, if the ultrasound probe is used over a long period of time, the layers adjacent to each other may be peeled from each other. If the layers are peeled from each other, it is difficult for the ultrasound probe to perform its function. When the sound pressure generated is relatively low, the peeling of layers from each other is not a problem because the workload of the piezoelectric element is small. However, particularly when a high pressure sound is generated, the peeling markedly occurs because the workload of the piezoelectric element is increased.

An acoustic impedance of the unimorph-type probe is generally about $4 \times 10^6$ kg/m$^2$ s to about $10 \times 10^6$ kg/m$^2$ s which is much lower than the acoustic impedance of the conventional probe using a bulk piezoelectric substance formed of an inorganic material. However, the acoustic impedance is higher than the acoustic impedance of a living body as a subject of an ultrasound diagnosis, which is about $1.5 \times 10^6$ kg/m$^2$ s. Accordingly, if the unimorph-type probe is used as is to make an ultrasound diagnosis, transmittance of an ultrasonic beam transmitted to the living body is reduced. Particularly, although the unimorph-type probe is suited for being prepared by microfabrication, it cannot easily realize a high sound pressure and high reception sensitivity. Moreover, the reduction in the transmittance of the ultrasonic beam resulting from the mismatching of the acoustic impedance causes a significant problem in making a highly accurate ultrasound diagnosis.

As described above, hitherto, nothing has been known regarding how the structure of the unimorph-type probe should be designed considering the application thereof to the ultrasound diagnosis, and thus a solution to the problem is required.

SUMMARY OF THE INVENTION

The present invention has been made to solve the aforementioned conventional problems, and an object thereof is to provide a unimorph-type ultrasound probe, which makes it possible to make an excellently reliable ultrasound diagnosis with high accuracy over a long period of time, and a method for manufacturing the unimorph-type ultrasound probe.

A unimorph-type ultrasound probe according to the present invention comprises a substrate in which a plurality of openings each having a predetermined shape is formed, a plurality of vibration plates formed on the substrate so as to close one end of each of the plurality of openings, a plurality of piezoelectric element portions which is formed on a surface of the plurality of vibration plates and each has a piezoelectric substance layer and a pair of electrode layers formed on both surfaces of the piezoelectric substance layer, and a covering layer which is disposed on a surface of the substrate such that the plurality of piezoelectric element portions is embedded in the covering layer, and is formed of an organic resin having an acoustic impedance of $1.5 \times 10^6$ kg/m$^2$ s to $4 \times 10^6$ kg/m$^2$ s and a Shore A hardness of equal to or less than 75.

According to the present invention, a covering layer formed of an organic resin having an acoustic impedance of $1.5 \times 10^6$ kg/m$^2$ s to $4 \times 10^6$ kg/m$^2$ s and a Shore A hardness equal to or less than 75 is disposed on a surface of a substrate such that a plurality of piezoelectric element portions is embedded in the covering layer. Consequently, each of the piezoelectric element portions is protected by the covering layer, and transmittance of an ultrasonic beam transmitted to a living body is improved. As a result, even when the present invention is applied to an ultrasound diagnosis for a living body in which a high sound pressure is required, a highly accurate ultrasound diagnosis can be made over a long period time with excellent reliability.

BRIEF DESCRIPTION OF THE DRAWINGS

FIGS. 8A and 8B show waveforms of residual vibration of organic resin materials.

DETAILED DESCRIPTION OF THE INVENTION

Hereinafter, embodiments of the present invention will be described based on the attached drawings.

Figure 1:
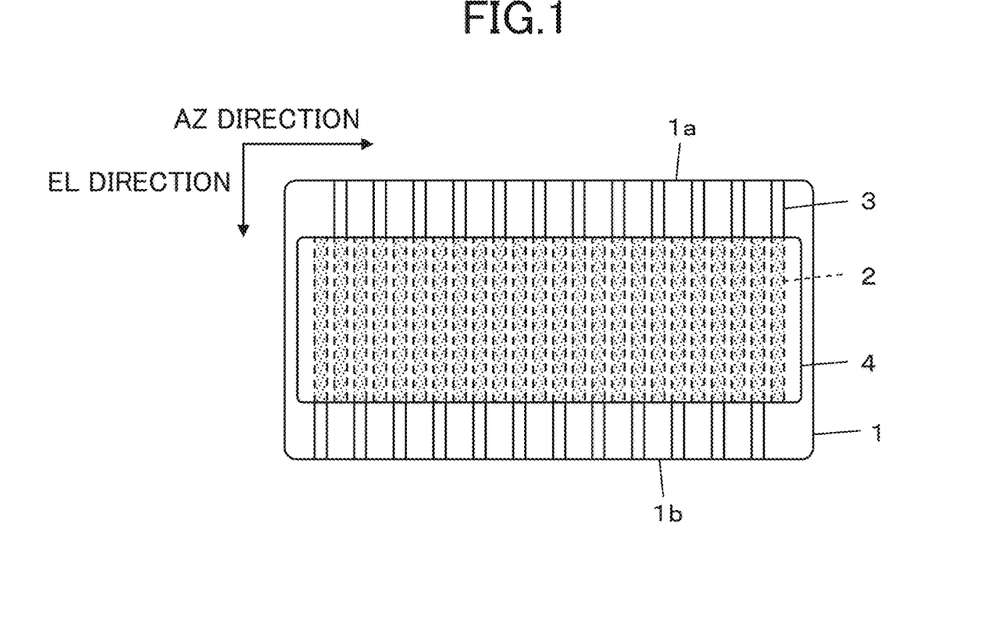
FIG. 1 is a plan view showing the constitution of a unimorph-type ultrasound probe according to an embodiment of the present invention.

FIG. 1 shows the constitution of a unimorph-type ultrasound probe according to an embodiment of the present invention.

In the unimorph-type ultrasound probe, a plurality of piezoelectric element regions 2 is formed on a surface of a substrate 1. Each of the piezoelectric element regions 2 extends in the form of a strip in an elevation (EL) direction, and is arranged at a small interval in an azimuth (AZ) direction. In each of the piezoelectric element regions 2, a plurality of minute piezoelectric element portions is formed and arranged. Furthermore, each of the piezoelectric element regions 2 is connected to a corresponding lead-out electrode 3 in the elevation direction. The lead-out electrodes 3 alternately extend in any one of a pair of lateral edges 1a and 1b of the substrate 1 so as to ensure an arrangement pitch therebetween.

Moreover, a covering layer 4 is disposed on the substrate 1 so as to cover all of the piezoelectric element regions 2.

Figure 2:
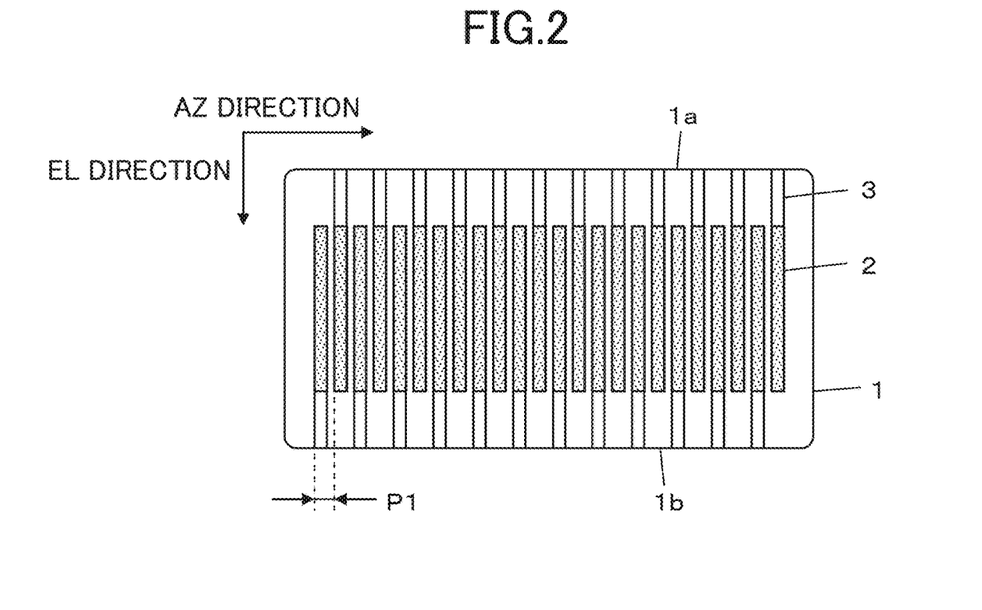
FIG. 2 is a plan view showing the unimorph-type ultrasound probe according to the embodiment from which a covering layer has been removed.

FIG. 2 showing the state in which the covering layer 4 has been removed clearly shows the plurality of piezoelectric element regions 2 each of which extends in the elevation direction. The piezoelectric element regions 2 are arranged in an azimuth direction with a pitch P1 of 250 μm, for example.

Figure 3:
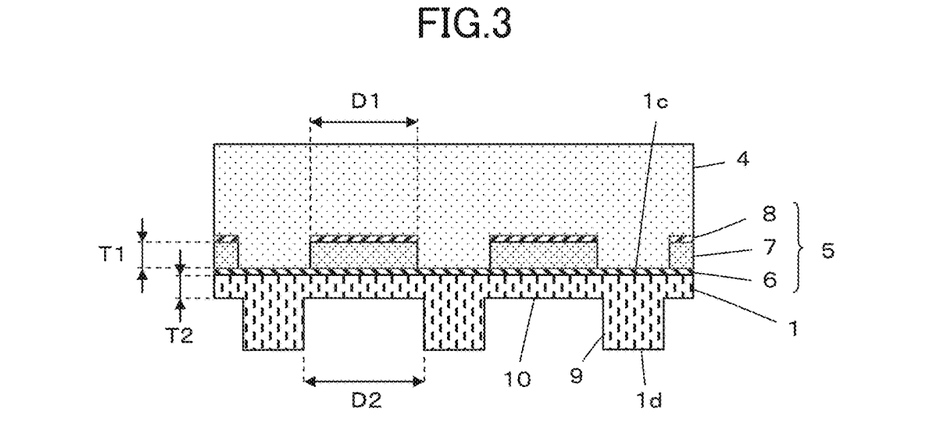
FIG. 3 is a cross-sectional view showing main portions of the unimorph-type ultrasound probe according to the embodiment.

As shown in FIG. 3, each of the plurality of minute piezoelectric element portions 5 arranged in the piezoelectric element regions 2 has a lower electrode layer 6 that is formed on a surface 1c of the substrate 1, a piezoelectric substance layer 7 having a thickness T1 that is formed on the lower electrode layer 6, and a upper electrode layer 8 that is formed on the piezoelectric substance layer 7. The piezoelectric substance layer 7 has a regular hexagonal plane shape, and the upper electrode layer 8 is formed to be the same regular hexagonal shape as the piezoelectric substance layer 7.

Figure 4:
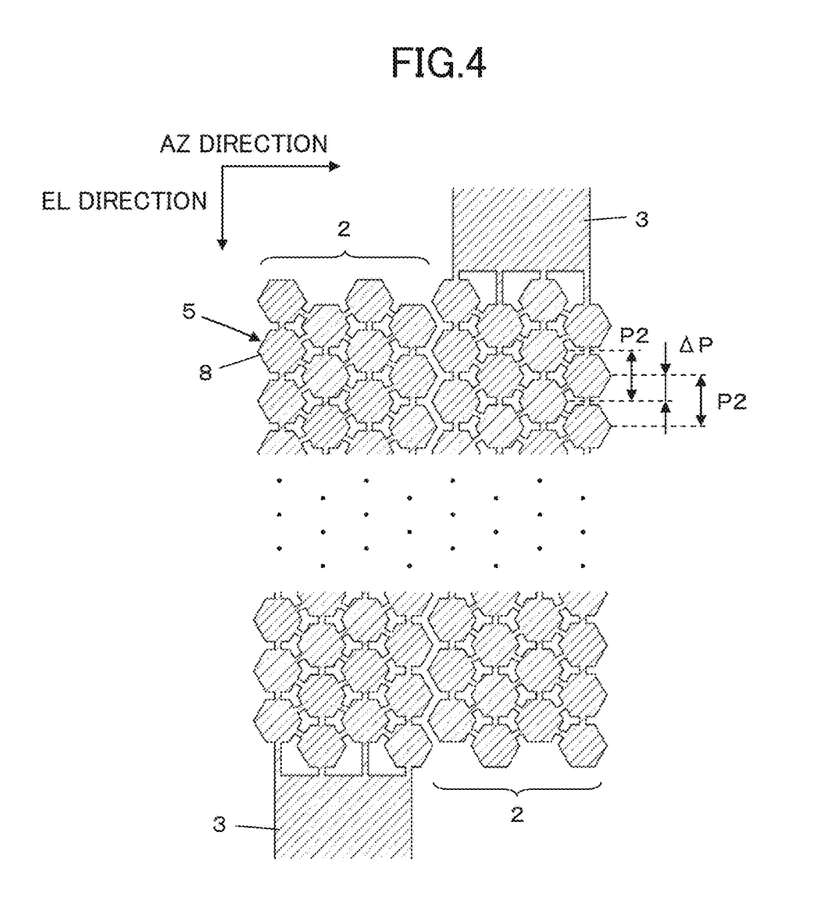
FIG. 4 is a partially enlarged plan view of the unimorph-type ultrasound probe according to the embodiment that shows two piezoeltric element regions adjacent to each other and a lead electrode connected to the piezoelectric element regions.

As shown in FIG. 4, the piezoelectric element portions 5 are disposed so as to have a close-packed structure. In the close-packed structure, the piezoelectric element portions 5 are arranged in the form of straight lines at a predetermined pitch P2 in the elevation direction of the probe to form a plurality of lines, and they deviate from each other in the elevation direction by deviation amount ΔP=P2/2 that is ½ of the pitch P2 in each of the lines. In addition, the upper electrode layers 8 of the piezoelectric element portions 5 formed in the same piezoelectric element region 2 are connected to each other and connected to the corresponding lead-out electrode 3. Herein, the lower electrode layers 6 of the piezoelectric element portions 5 formed and arranged in all of the piezoelectric element regions 2 are united as one by being connected to each other and thus form one sheet of an electrode layer on the surface 1c of the substrate 1.

That is, the piezoelectric substance layers 7 are separated for every piezoelectric element portions 5, the upper electrode layers 8 are united as one by being connected to each other in the same piezoelectric element region 2 and connected to the lead-out electrode 3, and the lower electrode layer 6 is common to all of the piezoelectric element portions 5 of all of the piezoelectric element regions 2.

As shown in FIG. 3, on the side of a rear surface 1d of the substrate 1 corresponding to the arrangement positions of the respective piezoelectric element portions 5, openings 9 are formed. Due to the formation of the openings 9, the substrate 1 becomes thin, and vibration plates 10 having a thickness T2 are formed on the side of the surface 1c of the substrate 1 so as to close one end of the openings 9. Each of the piezoelectric element portions 5 is arranged on the corresponding vibration plate 10.

Each of the openings 9 has a shape similar to the shape of the piezoelectric substance layer 7 of the corresponding piezoelectric element portion 5, and has a regular hexagonal plane shape that is the same as or larger than the plane shape of the piezoelectric substance layer 7. That is, provided that the average of a diameter of an inscribed circle of the regular hexagon and a diameter of a circumscribed circle of the regular hexagon is called a diameter of the regular hexagon, a diameter D2 of the opening 9 is equal to or greater than a diameter D1 of the piezoelectric substance layer 7 of the piezoelectric element portion 5, and the piezoelectric substance layer 7 is formed on a surface of the vibration plate 10 so as not to extend beyond the peripheral edge of the vibration plates 10. If such a constitution is adopted, the vibration plate 10 can easily vibrate along with the vibration generated in the piezoelectric element portions 5, and it is possible to increase sound pressure by efficiently transmitting ultrasonic waves. Herein, in the probe shown in FIG. 3, the diameter D2 of the opening 9 is set to be greater than the diameter D1 of the piezoelectric substance layer 7.

All of the piezoelectric element portions 5 formed on the substrate 1 are covered with the covering layer 4. The covering layer 4 is filled up to the lateral surface portion of each of the piezoelectric substance layers 7 such that each of the piezoelectric element portions 5 is embedded in the covering layer 4. The covering layer 4 is formed of an organic resin having an acoustic impedance of $1.5 \times 10^6$ $kg/m^2$ s to $4 \times 10^6$ $kg/m^2$ s (1.5 Mrayl to 4 Mrayl) and a Shore A hardness of equal to or less than 75. The covering layer 4 has a thickness that satisfies a sound matching condition, that is, a ¼ wavelength condition at the frequency used by the unimorph-type ultrasound probe.

Each of the piezoelectric element portions 5 is protected by being embedded in the covering layer 4. Accordingly, even though the unimorph-type ultrasound probe is driven at a high speed for a long period time in a MHz band suited for an ultrasound diagnosis, the layers in the piezoelectric element portion 5 are previously prevented from being peeled from each other, and a highly reliable ultrasound diagnosis can be made.

Furthermore, the covering layer 4 has an acoustic impedance of $1.5 \times 10^6$ kg/m$^2$ s to $4 \times 10^6$ kg/m$^2$ s which is close to an acoustic impedance of a living body which may be the subject of the ultrasound diagnosis. Accordingly, it is possible to inhibit the reduction in the transmittance of the ultrasonic beam transmitted to the living body and to obtain a high-accuracy ultrasound diagnostic image.

For example, the unimorph-type ultrasound probe according to the present embodiment can be manufactured as below.

Figure 5A:
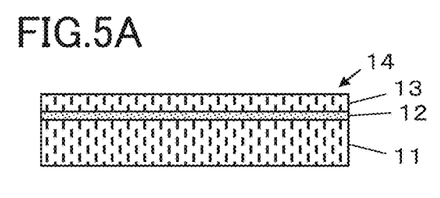
FIGS. 5A to 5J are cross-sectional views showing a method for manufacturing a unimorph-type ultrasound probe according to an embodiment of the present invention in order of steps.

First, as shown in FIG. 5A, an SOI substrate 14 is prepared in which a monocrystalline Si layer 13 having a thickness of several μm is formed on a Si base material 11 having a thickness of about 500 μm and formed of monocrystalline Si via a thermally oxidized SiO$_2$ film 12 having a thickness of 1 μm to 2 μm that is to be an insulating layer.

Figure 5B:
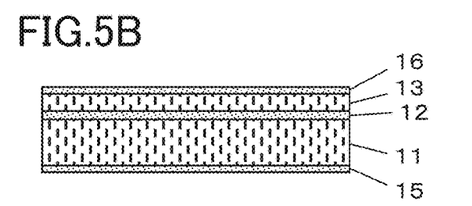

Then, as shown in FIG. 5B, for the purpose of preventing diffusion of Pb to the Si base material 11 and the monocrystalline Si layer 13 or the like, on both surfaces of the SOI substrate 14, thermally oxidized SiO$_2$ films 15 and 16 each having a thickness of about 0.3 μm are formed.

Figure 5C:
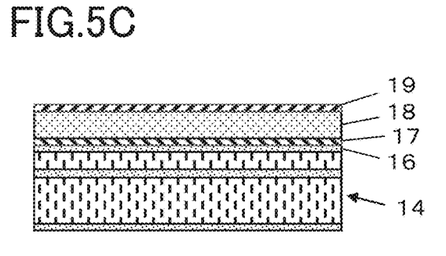

Thereafter, as shown in FIG. 5C, on the thermally oxidized SiO$_2$ film 16, an electrode layer 17, which is formed of Ti having a thickness of 30 nm and Pt having a thickness of 150 nm, is formed by a sputtering method. On the electrode layer 17, a PZT film 18 having a thickness of 1 μm to 10 μm is formed by a sputtering method. Furthermore, on the PZT film 18, an electrode layer 19, which is formed of Ti having a thickness of 30 nm and Pt having a thickness of 150 nm, is formed by a sputtering method.

Figure 5D:
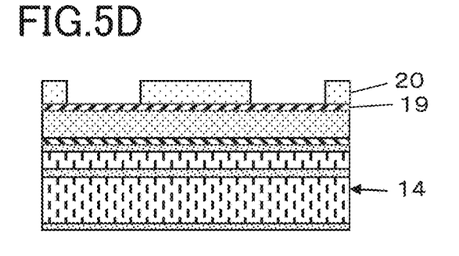

As shown in FIG. 5D, a resist is applied onto the electrode layer 19 as an uppermost layer, cured, exposed to light through a UV mask, and then developed. In this way, an upper mask 20 is formed which corresponds to the upper electrode layer 8 of the piezoelectric element portion 5 that is to be prepared from now on.

Figure 5E:
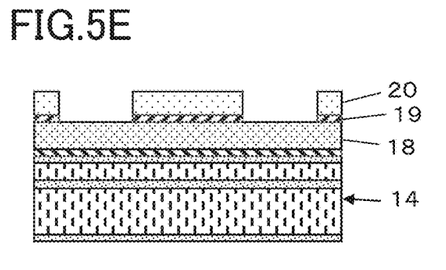
Figure 5F:
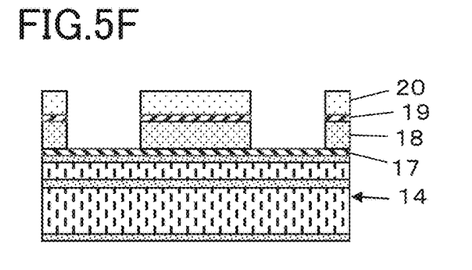

Moreover, as shown in FIG. 5E, by means of reactive ion etching, the electrode layer 19 in the portions exposed through the upper mask 20 is removed. In addition, as shown in FIG. 5F, the PZT film 18 in the portions exposed through the upper mask 20 is removed by etching.

Figure 5G:
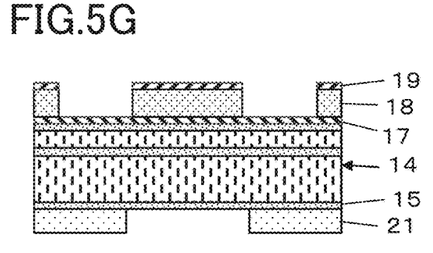

Subsequently, as shown in FIG. 5G, the upper mask 20 is removed by using a remover, and a resist is applied onto the bottom surface of the thermally oxidized SiO$_2$ film 15 as the lowermost layer, cured, exposed to light through a UV mask, and then developed. In this way, a rear surface mask 21 is formed which corresponds to the openings 9 of the substrate 1 that is to be prepared from now on.

Figure 5H:
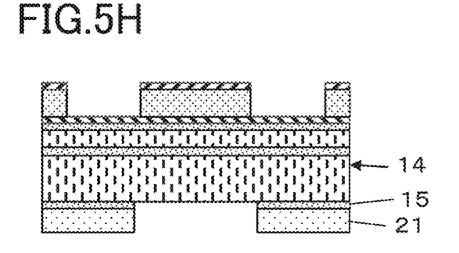
Figure 5I:
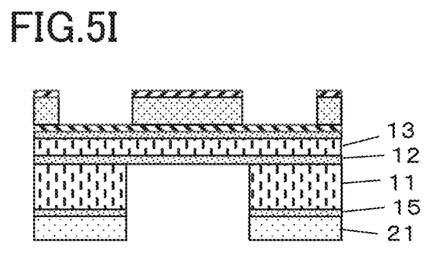
Figure 5J:
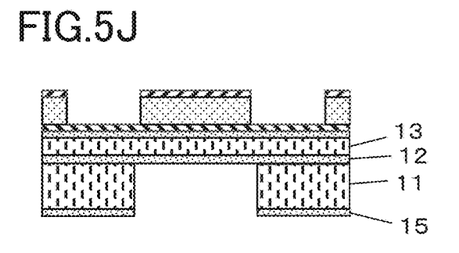

Next, as shown in FIG. 5H, by means of reactive ion etching, the thermally oxidized SiO$_2$ film 15 in the portions exposed through the rear surface mask 21 is removed. In addition, as shown in FIG. 5I, the Si base material 11 of the SOI substrate 14 in portions exposed through the rear surface mask 21 is removed by deep dry etching. At this time, the thermally oxidized SiO$_2$ film 12 of the SOI substrate 14 functions as an etch-stop layer, and the Si base material 11 is hollowed out in a shape formed by the rear surface mask 21 such that the thermally oxidized SiO$_2$ film 12 is exposed. Thereafter, as shown in FIG. 5J, the rear surface mask 21 is removed by using a remover.

The substrate 1 is formed of the Si base material 11, the thermally oxidized SiO$_2$ film 12, and the monocrystalline Si layer 13, and the vibration plate 10 is formed of the thermally oxidized SiO$_2$ film 12 and the monocrystalline Si layer 13. Furthermore, the lower electrode layer 6 is formed of the electrode layer 17, the piezoelectric substance layer 7 is formed of the PZT film 18, and the upper electrode layer 8 is formed of the electrode layer 19.

Figure 6:
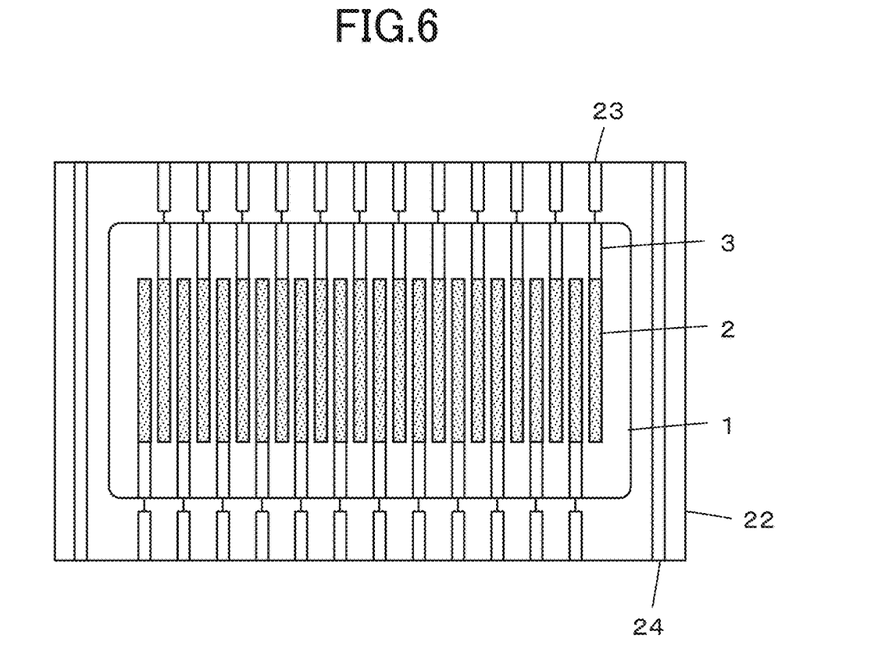
FIG. 6 is a plan view showing a state in which the unimorph-type ultrasound probe according to the embodiment is mounted on FPC.

In this way, a probe without the covering layer 4 is prepared as shown in FIG. 2. Furthermore, as shown in FIG. 6, such a probe is mounted on a FPC (flexible printed circuit) 22 or the like, each of the plurality of lead-out electrodes 3 is connected to a corresponding wiring pattern 23 of the FPC 22, and the lower electrode layer 6 common to all of the piezoelectric element portions 5 is connected to a ground pattern 24 of the FPC 22. The connection can be performed by using Ag paste, wire bonding, low-temperature soldering, and the like.

Thereafter, the covering layer 4 is formed on the substrate 1 by means of coating so as to cover all of the piezoelectric element regions 2, and in this way, the manufacturing process of the unimorph-type ultrasound probe ends.

Through experiments, it was known that in order to generate a high-accuracy ultrasound image, a transmission sound pressure equal to or greater than approximately 50 kPa is generally required.

Therefore, first, the diameter D2 of the opening 9 of the substrate 1 and the thickness T1 of the piezoelectric substance layer 7 were variously combined, and for each of the combinations, the values of the transmission sound pressure, which were obtained by varying the thickness T2 of the vibration plate 10, were measured. As a result, it was found that regardless of the value of the diameter D2 of the opening 9 and the value of the thickness T1 of the piezoelectric substance layer 7, the transmission sound pressure is maximized when a ratio of the thickness T2 of the vibration plate 10 to the thickness T1 of the piezoelectric substance layer 7 is 0.8 to 1.2, and the transmission sound pressure decreases from the maximum value even if the ratio is less than 0.8 or greater than 1.2.

Figure 7:
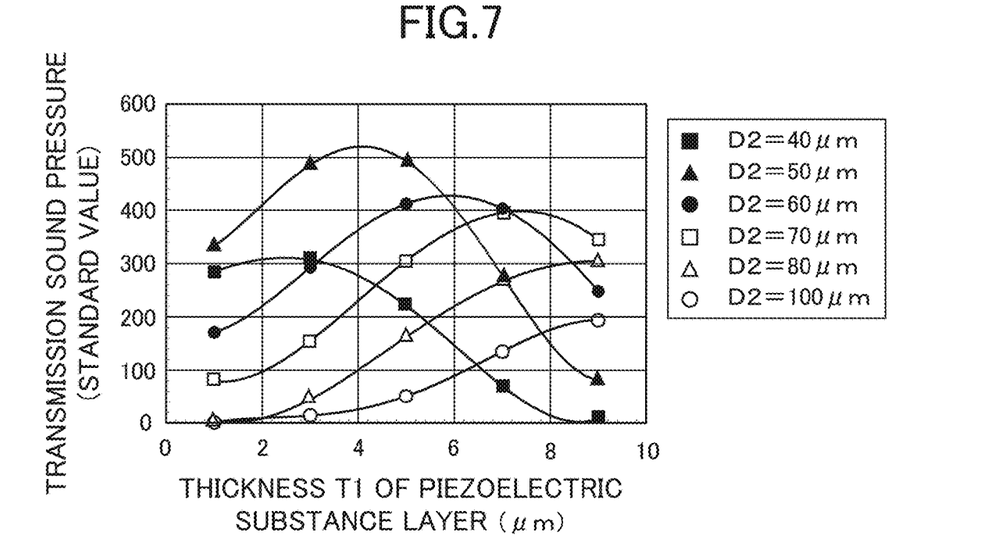
FIG. 7 is a graph showing a relationship between a thickness of a piezoelectric substance layer and a transmission sound pressure that is established when the diameter of openings of a substrate is varied.

Then, the ratio of the thickness T1 of the piezoelectric substance layer 7 to the thickness T2 of the vibration plate 10 was kept at 1:0.8 to 1:1.2, and by FEM (finite element method) simulation, relationships between the thickness T1 of the piezoelectric substance layer 7 and the transmission sound pressure, that were established when the diameter D2 of the opening 9 of the substrate 1 was variously varied within a range of 40 μm to 100 μm, were measured. As a result, the results shown in FIG. 7 were obtained. Herein, the ordinate in FIG. 7 represents values of standardized transmission sound pressure. For example, a standardized value of 500 to 600 corresponds to sound pressure of about 100 kPa.

From FIG. 7, it is understood that the greater the diameter D2 of the opening 9, the greater the thickness T1 of the piezoelectric substance layer 7 showing a peak value of the transmission sound pressure. For example, the transmission sound pressure in a case in which the diameter D2 of the opening 9 is equal to 50 μm reaches the peak value when the thickness T1 of the piezoelectric substance layer 7 is equal to about 4 μm, and the transmission sound pressure in a case in which the diameter D2 of the opening 9 is equal to 80 μm reaches the peak value when the thickness T1 of the piezoelectric substance layer 7 is equal to about 9 μm.

It is also understood that the peak value of the transmission sound pressure relating to the diameter D2 of each of the openings 9 is maximized when the diameter D2 of the opening 9 is equal to 50 μm, and even if the diameter D2 becomes smaller or greater than 50 μm, the peak value is gradually reduced. For example, the transmission sound pressure in a case in which the diameter D2 of the opening 9 is equal to 50 μm has a peak greater than the standard value of 500, and when the diameter D2 of the opening 9 becomes equal to 100 μm, a peak of a standard value of approximately 200 is merely obtained.

As a result of investigating a relationship between the standard value of the transmission sound pressure shown in the ordinate in FIG. 7 and a level of performance of the probe through experiments, it was found that, as shown in the following Table 1, the probe can be classified by evaluation into 5 levels from level AA to level D according to the standard value of the transmission sound pressure.

TABLE 1

| Evaluation | Transmission sound pressure (standard value) | Description |
|---|---|---|
| AA | Equal to or greater than 400 | High level of performance for being used as probe of ultrasound diagnostic apparatus |
| A | Equal to or greater than 300 and less than 400 | Level for being put to practical use as probe of ultrasound diagnostic apparatus |
| B | Equal to or greater than 200 and less than 300 | Level for being able to be put to practical use as probe for capturing simple ultrasound image |
| C | Equal to or greater than 100 and less than 200 | Level for being able to be put to practical use as probe for sensing |
| D | Less than 100 | Equal to or lower than level for being put to practical use |

That is, when the standard value of the transmission sound pressure is equal to or greater than 400, the probe is evaluated to be "AA" because it has a high level of performance as a probe of an ultrasound diagnostic apparatus, and when the standard value of the transmission sound pressure is equal to or greater than 300 and less than 400, the probe is evaluated to be "A" because it performs at a practical level as a probe of an ultrasound diagnostic apparatus. When the standard value of the transmission sound pressure is equal to or greater than 200 and less than 300, the probe is evaluated to be "B" because it performs at a level of being able to put to practical use for obtaining a simple ultrasound image.

In contrast, when the standard value of the transmission sound pressure is less than 200, it is difficult to obtain an ultrasound image that can be put to practical use. When the standard value of the transmission sound pressure is equal to or greater than 100 and less than 200, the probe is evaluated to be "C" because it performs at a level of being able to put to practical use for sensing. When the standard value of the transmission sound pressure is less than 100, the probe is evaluated to be "D" because it performs at a level equal to or lower than a level of being used for sensing.

By reading out the standard value of the transmission sound pressure for each combination of the diameter D2 of the opening 9 and the thickness T1 of the piezoelectric substance layer 7 from the graph of FIG. 7, the evaluation results shown in the following Table 2 and Table 3 can be obtained.

TABLE 2

| Diameter D2 of opening (μm) | Thickness T1 of piezoelectric substance layer (μm) | Thickness T2 of vibration plate (μm) | Evaluation |
|---|---|---|---|
| 40 | 1 | T1 × (1 ± 0.2) | B |
|  | 2 | T1 × (1 ± 0.2) | A |
|  | 3 | T1 × (1 ± 0.2) | A |
|  | 4 | T1 × (1 ± 0.2) | B |
|  | 5 | T1 × (1 ± 0.2) | B |
|  | 6 | T1 × (1 ± 0.2) | C |
|  | 7 | T1 × (1 ± 0.2) | D |
|  | 8 | T1 × (1 ± 0.2) | D |
|  | 9 | T1 × (1 ± 0.2) | D |
| 50 | 1 | T1 × (1 ± 0.2) | A |
|  | 2 | T1 × (1 ± 0.2) | AA |
|  | 3 | T1 × (1 ± 0.2) | AA |
|  | 4 | T1 × (1 ± 0.2) | AA |
|  | 5 | T1 × (1 ± 0.2) | AA |
|  | 6 | T1 × (1 ± 0.2) | AA |
|  | 7 | T1 × (1 ± 0.2) | B |
|  | 8 | T1 × (1 ± 0.2) | C |
|  | 9 | T1 × (1 ± 0.2) | D |
| 60 | 1 | T1 × (1 ± 0.2) | C |
|  | 2 | T1 × (1 ± 0.2) | B |
|  | 3 | T1 × (1 ± 0.2) | B |
|  | 4 | T1 × (1 ± 0.2) | A |
|  | 5 | T1 × (1 ± 0.2) | AA |
|  | 6 | T1 × (1 ± 0.2) | AA |
|  | 7 | T1 × (1 ± 0.2) | AA |
|  | 8 | T1 × (1 ± 0.2) | A |
|  | 9 | T1 × (1 ± 0.2) | B |

TABLE 3

| Diameter D2 of opening (μm) | Thickness T1 of piezoelectric substance layer (μm) | Thickness T2 of vibration plate (μm) | Evaluation |
|---|---|---|---|
| 70 | 1 | T1 × (1 ± 0.2) | D |
|  | 2 | T1 × (1 ± 0.2) | D |
|  | 3 | T1 × (1 ± 0.2) | C |
|  | 4 | T1 × (1 ± 0.2) | B |
|  | 5 | T1 × (1 ± 0.2) | A |
|  | 6 | T1 × (1 ± 0.2) | A |
|  | 7 | T1 × (1 ± 0.2) | A |
|  | 8 | T1 × (1 ± 0.2) | A |
|  | 9 | T1 × (1 ± 0.2) | A |
| 80 | 1 | T1 × (1 ± 0.2) | D |
|  | 2 | T1 × (1 ± 0.2) | D |
|  | 3 | T1 × (1 ± 0.2) | D |
|  | 4 | T1 × (1 ± 0.2) | C |
|  | 5 | T1 × (1 ± 0.2) | C |
|  | 6 | T1 × (1 ± 0.2) | B |
|  | 7 | T1 × (1 ± 0.2) | B |
|  | 8 | T1 × (1 ± 0.2) | B |
|  | 9 | T1 × (1 ± 0.2) | A |
| 100 | 1 | T1 × (1 ± 0.2) | D |
|  | 2 | T1 × (1 ± 0.2) | D |
|  | 3 | T1 × (1 ± 0.2) | D |
|  | 4 | T1 × (1 ± 0.2) | D |
|  | 5 | T1 × (1 ± 0.2) | D |
|  | 6 | T1 × (1 ± 0.2) | D |
|  | 7 | T1 × (1 ± 0.2) | C |
|  | 8 | T1 × (1 ± 0.2) | C |
|  | 9 | T1 × (1 ± 0.2) | C |

As is evident from the tables, based on the evaluation results, as combinations of the diameter D2 of the opening 9 and the thickness T1 of the piezoelectric substance layer 7, T1 is set to be 1 μm to 5 μm when D2=40 μm, set to be 1 μm to 7 μm when D2=50 μm, set to be 2 μm to 9 μm when D2=60 μm, set to be 4 μm to 10 μm when D2=70 μm, and set to be 6 μm to 10 μm when D2=80 μm. In this way, the probe is evaluated to be one of "AA", "A", and "B", and it is possible to obtain ultrasound images at a level which is equal to or higher than a level of being able to put to practical use.

In FIG. 7, the transmission sound pressure with respect to the thickness T1 of the piezoelectric substance layer 7 that is equal to 1 μm to 9 μm is shown, but measurement points with respect to the thickness T1 of the piezoelectric substance layer 7 that is equal to 10 μm are not plotted. However, from a characteristic curve with respect to the diameter D2 of each of the openings 9, the entirety of the transmission sound pressure at the time when D2=70 μm and T1=10 μm and the transmission sound pressure at the time when D2=80 μm and T1=10 μm are expected to exceed a standard value of 200. Therefore, the combination of D2=70 μm and T1=10 μm and the combination of D2=80 μm and T1=10 μm are also included in the above combinations which make it possible to obtain ultrasound images at a level which is equal to or higher than a level of being able to be put to practical use.

Furthermore, when T1 is set to be 2 μm to 3 μm when D2=40 μm, set to be 1 μm to 6 μm when D2=50 μm, set to be 4 μm to 8 μm when D2=60 μm, set to be 5 μm to 9 μm when D2=70 μm, and set to be 9 μm when D2=80 μm, all of the probes are evaluated to be "AA" or "A" and perform at a high-performance level or a practical level as probes of an ultrasound diagnostic apparatus.

Regarding piezoelectric elements used in an ink jet and the like, a structure in which a piezoelectric substance is formed on a vibration plate is known. Generally, the diameter of the vibration plate is much greater than 100 μm, and the relationship, which is shown in FIG. 7, between the element structure for transmitting ultrasonic waves using the vibration plate having a diameter of equal to or less than 100 μm and the sound pressure has been revealed for the first time by the examination conducted for making the invention for the present application. Through the examination, it was clearly revealed that there is a structure that can obtain a high sound pressure capable of being put to practical use in an ultrasound diagnostic apparatus even when the diameter of the vibration plate is equal to or less than 100 μm.

Figure 8A:
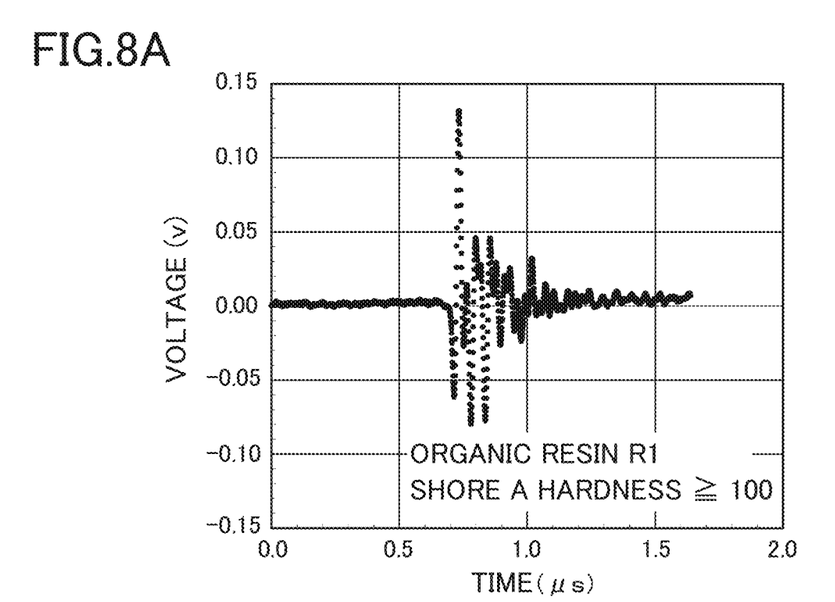
FIG. 8A shows a waveform of an organic resin material having a Shore A hardness of equal to or greater than 100.
Figure 8B:
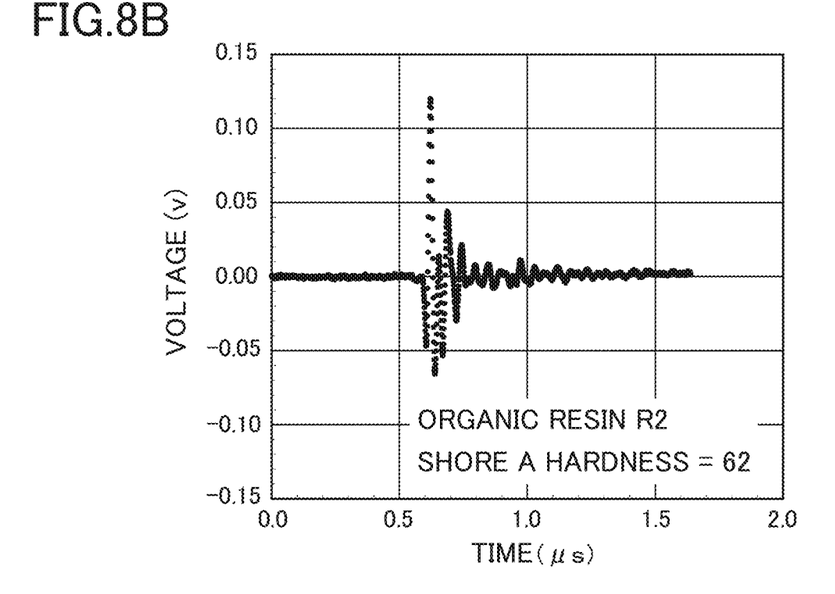
FIG. 8B shows a waveform of an organic resin material having a Shore A hardness of 62.

For examining organic resin materials used in the covering layer 4, FIGS. 8A and 8D show waveforms of residual vibration of two kinds of organic resins differing from each other in terms of a Shore A hardness. FIG. 8A shows a waveform of an organic resin R1 (Epoxy 301-2FL manufactured by Epoxy Technology, Inc) having a Shore A hardness of equal to or greater than 100, and FIG. 8B shows a waveform of an organic resin R2 (Epoxy 301M manufactured by Epoxy Technology, Inc) having a Shore A hardness of 62. Comparing the organic resins R1 and R2 to each other, while the residual vibration remains for a long period of time in the organic resin R1 having a greater Shore A hardness, the residual vibration is attenuated within a short period of time in the organic resin R2 having a small Shore A hardness.

If the next ultrasonic wave is transmitted at the timing when significant residual vibration remains, a wavefront of the transmitted beam is disturbed, and thus a highly accurate ultrasound diagnosis cannot be easily made. If a transmission frequency of an ultrasonic wave is set to be 10 MHz, a period becomes 0.1 μs. It is desirable that the residual vibration is attenuated to some extent within a time period that is equal to about 0.1 μs.

Figure 9:
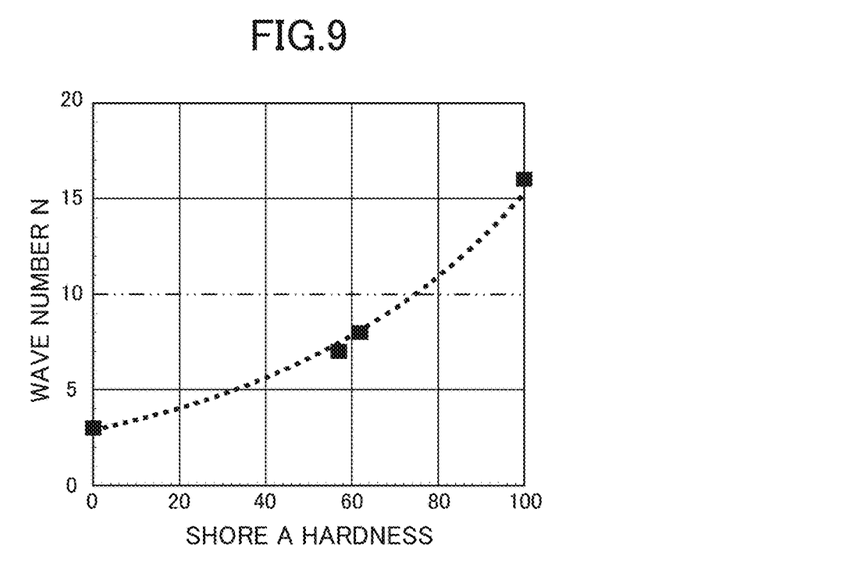
FIG. 9 is a graph showing a relationship between the Shore A hardness of an organic resin material and the wave number of residual vibration thereof.

A wave number N, in which a voltage intensity became equal to or greater than 10% of a value of maximum peak voltage of the residual vibration, was determined. As a result, it was found that N was equal to 16 in the organic resin R1 shown in FIG. 8A and was equal to 8 in the organic resin R2 shown in FIG. 8B. Likewise, as a result of determining the wave number N for a silicone resin having a Shore A hardness of 57, it was found that N was equal to 7. If a relationship between the Shore A hardness of the organic resin and the wave number N of the organic resin is described including the silicone resin, the graph of FIG. 9 is obtained. Ideally, due to its structure, the unimorph-type ultrasound probe without the covering layer 4 has a residual vibration of 3 waves. Therefore, in FIG. 9, a wave number of N=3 is plotted for a Shore A hardness of 0. As the Shore A hardness of a resin material increases, the wave number N, in which a voltage intensity becomes equal to or greater than 10% of a value of maximum peak voltage of the residual vibration, tends to increase.

Herein, with an organic resin material such as the organic resin R1 shown in FIG. 8A having the wave number N, in which a voltage intensity becomes equal to or greater than 10% of a value of maximum peak voltage of the residual vibration, of greater than 10, a frequency band suited for an ultrasound diagnosis may not be able to be set. Consequently, such a resin is inappropriate as a material for the covering layer 4.

In contrast, if an organic resin material such as the organic resin R2 shown in FIG. 8B having the wave number N, in which a voltage intensity becomes equal to or greater than 10% of a value of maximum peak voltage of the residual vibration, of equal to or less than 10 is used as the covering layer 4, it is possible to set a frequency band in which an ultrasound diagnosis can be sufficiently made. The Shore A hardness of such a resin material read out from FIG. 9 is equal to or less than 75.

Therefore, in the present invention, as the material of the covering layer 4, an organic resin having a Shore A hardness of equal to or less than 75 is used.

If all of the piezoelectric element portions 5 are covered with such a covering layer 4, the piezoelectric element portions 5 can be mechanically protected, and at the same time, a highly accurate ultrasound diagnosis can be made by driving the unimorph-type ultrasound probe in a MHz band suited for the ultrasound diagnosis.

The lower limit of the Shore A hardness of the organic resin material used as the covering layer 4 is not particularly limited. However, for example, if the Shore A hardness is about equal to or greater than 20, it is possible to prevent the layers in the piezoelectric element portion 5 from being peeled from each other by sufficiently protecting the piezoelectric element portion 5.

Figure 10:
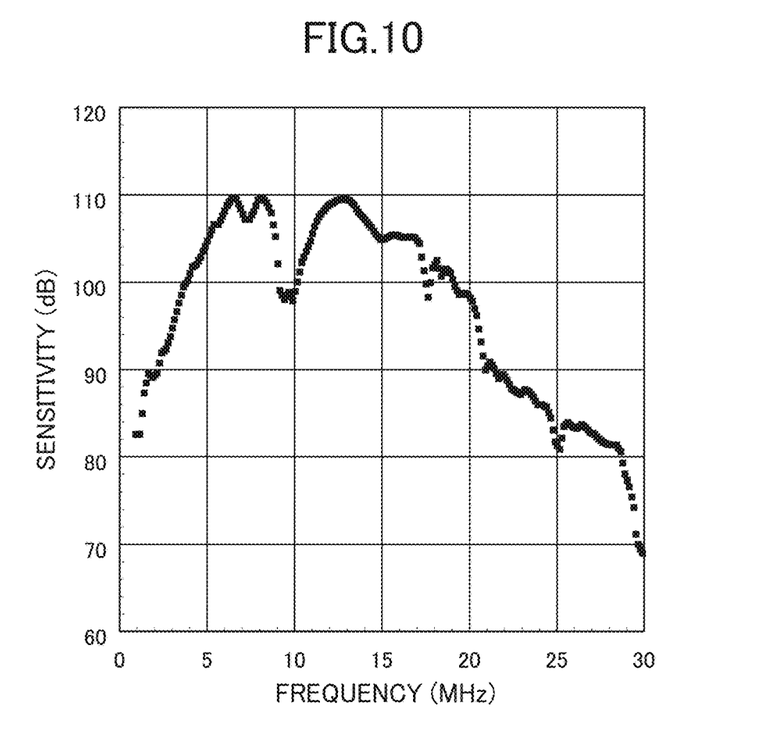
FIG. 10 is a graph showing a relationship between a frequency of the unimorph-type ultrasound probe according to the embodiment and the sensitivity thereof.

A 64-channel unimorph-type ultrasound probe was manufactured by setting the diameter D2 of the opening 9 to be equal to 70 μm, setting the thickness of T1 of the piezoelectric substance layer 7 to be 7 μm, and setting the ratio of the thickness T1 of the piezoelectric substance layer 7 to the thickness T2 of the vibration plate 10 to be 1:1.1, and a relationship between a frequency and sensitivity of the probe was measured in water in a 2-way manner of transmission and reception. As a result, the result shown in FIG. 10 was obtained.

A −6 dB band from a peak value of maximum sensitivity covered a frequency of about 4 MHz to 18 MHz, and this showed that the unimorph-type ultrasound probe covers an ultra-wideband that is extremely wide compared to the conventional probes.

Figure 11:
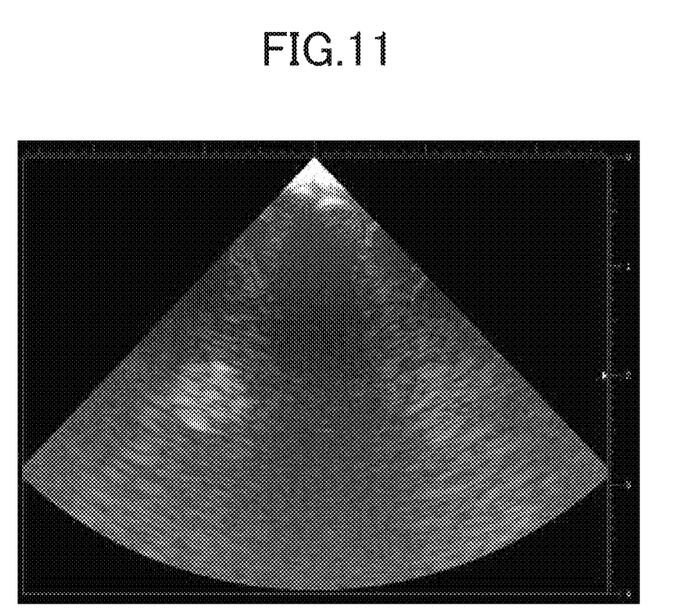
FIG. 11 is a photograph showing an ultrasound image captured by using the unimorph-type ultrasound probe according to the embodiment.

FIG. 11 shows an actual ultrasound image of an anechoic cyst captured by using the aforementioned 64-channel unimorph-type ultrasound probe. The image was captured up to a depth of 4 cm without using an acoustic lens by setting a driving voltage of the probe to be ±50 V. The image definitely shows that a high-accuracy clear ultrasound image can be obtained by the probe.

As shown in FIG. 4, in the unimorph-type ultrasound probe according to the aforementioned embodiment, the piezoelectric substance layer 7 and the upper electrode layer 8 of each of the piezoelectric element portions 5 have a regular hexagonal plane shape. However, the plane shape thereof is not limited thereto and may be a circular shape or a shape of a regular polygon other than a hexagon. In this case, it is preferable that the opening 9 of the substrate 1 also has a plane shape similar to the plane shape of the piezoelectric substance layer 7 and the upper electrode layer 8 of the piezoelectric element portions 5. When the regular polygonal shape is used, the same as in the case of the regular hexagon, the average of the diameter of an inscribed circle of the regular hexagon and the diameter of a circumscribed circle of the regular hexagon is called the diameter of the regular polygon.

Furthermore, regarding the unimorph-type ultrasound probe according to the aforementioned embodiment, a so-called 1D (dimensional) array in which the plurality of piezoelectric element regions 2 is arranged in the azimuth direction was exemplified. However, the present invention is not limited to the 1D array. For example, the unimorph-type ultrasound probe according to the present invention can be applied to a so-called 1.5D array, in which each of the piezoelectric element regions is also divided into approximately 3 to 5 plural regions in the elevation direction such that the ultrasonic beam can be adjusted stepwise in the depth direction, or to a so-called 2D array, in which each of the piezoelectric element regions is also divided into a large number of regions in the elevation direction such that the ultrasonic beam can be freely radiated in both of the azimuth direction and the elevation direction. Such 1.5D array or 2D array can be more easily prepared in the unimorph-type ultrasound probe of the present invention than in the ultrasound probe of the conventional model.

What is claimed is:

1. A unimorph-type ultrasound probe comprising:
   a substrate in which a plurality of piezoelectric element regions is formed, a plurality of openings each having a predetermined shape being formed in each of the plurality of piezoelectric element regions;
   a plurality of vibration plates formed in each of the plurality of piezoelectric element regions on the substrate so as to close one end of each of the plurality of openings;
   a plurality of piezoelectric element portions which is formed in each of the plurality of piezoelectric element regions on surfaces of the plurality of vibration plates and has a plurality of piezoelectric substance layers, a plurality of first electrode layers disposed on one surfaces of the plurality of piezoelectric substance layers, and a plurality of second electrode layers disposed on the other surfaces of the plurality of piezoelectric substance layers;
   a covering layer which is disposed on a surface of the substrate such that the plurality of piezoelectric element portions in each of the plurality of piezoelectric element regions is embedded in the covering layer, and is formed of an organic resin having an acoustic impedance of $1.5 \times 10^6$ kg/m$^2$ s to $4 \times 10^6$ kg/m$^2$ s and a Shore A hardness of equal to or less than 75; and
   a plurality of lead-out electrodes disposed on the surface of the substrate corresponding to the plurality of piezoelectric element regions,
   wherein the plurality of first electrode layers of the plurality of piezoelectric element portions formed in each of the plurality of piezoelectric element regions is united as one by being connected to each other and connected to a corresponding lead-out electrode.

2. The unimorph-type ultrasound probe according to claim 1,
   wherein the plurality of openings have a diameter of 40 μm to 80 μm,
   the piezoelectric substance layer has a thickness of 1 μm to 10 μm, and
   a ratio of the thickness of the piezoelectric substance layer to a thickness of the vibration plate is 1:0.8 to 1:1.2.

3. The unimorph-type ultrasound probe according to claim 2,
   wherein a combination of a value of the diameter of the plurality of openings and a value of the thickness of the piezoelectric substance layer is selected such that a transmission sound pressure becomes equal to or greater than a preset value.

4. The unimorph-type ultrasound probe according to claim 3,
   wherein the plurality of openings have a diameter of 40 μm, and the piezoelectric substance layer has a thickness of 1 μm to 5 μm.

5. The unimorph-type ultrasound probe according to claim 4,
   wherein the piezoelectric substance layer has a thickness of 2 μm to 3 μm.

6. The unimorph-type ultrasound probe according to claim 3,
   wherein the plurality of openings have a diameter of 50 μm, and the piezoelectric substance layer has a thickness of 1 μm to 7 μm.

7. The unimorph-type ultrasound probe according to claim 6,
   wherein the piezoelectric substance layer has a thickness of 1 μm to 6 μm.

8. The unimorph-type ultrasound probe according to claim 3,
   wherein the plurality of openings have a diameter of 60 μm, and the piezoelectric substance layer has a thickness of 2 μm to 9 μm.

9. The unimorph-type ultrasound probe according to claim 8,
   wherein the piezoelectric substance layer has a thickness of 4 μm to 8 μm.

10. The unimorph-type ultrasound probe according to claim 3,
    wherein the plurality of openings have a diameter of 70 μm, and the piezoelectric substance layer has a thickness of 4 μm to 10 μm.

11. The unimorph-type ultrasound probe according to claim 10,
    wherein the piezoelectric substance layer has a thickness of 5 μm to 9 μm.

12. The unimorph-type ultrasound probe according to claim 3,
    wherein the plurality of openings have a diameter of 80 μm, and the piezoelectric substance layer has a thickness of 6 μm to 10 μm.

13. The unimorph-type ultrasound probe according to claim 12,
    wherein the piezoelectric substance layer has a thickness of 9 μm.

14. The unimorph-type ultrasound probe according to claim 1,
wherein the substrate is an SOI substrate in which a Si layer is formed on a Si base material via an insulating layer, and
each of the plurality of vibration plates is composed of the Si layer in a portion corresponding to the plurality of openings, which is formed by hollowing out the Si base material in a predetermined shape so as to make the insulating layer exposed, and the insulating layer.

15. The unimorph-type ultrasound probe according to claim 1,
wherein the predetermined shape of the plurality of openings is a circle or a regular polygon.

16. The unimorph-type ultrasound probe according to claim 1,
wherein the plurality of piezoelectric element portions is formed on surfaces of corresponding vibration plates so as not to extend beyond peripheral edges of the corresponding vibration plates.

17. The unimorph-type ultrasound probe according to claim 1,
wherein the plurality of piezoelectric element portions in each of the plurality of piezoelectric element regions is disposed so as to have a close-packed structure in which the piezoelectric element portions are arranged in the form of straight lines at a predetermined pitch in an elevation direction to form a plurality of lines, and the piezoelectric element portions deviate from each other in a deviation amount that is ½ of the predetermined pitch in each of the plurality of lines.

18. The unimorph-type ultrasound probe according to claim 1,
wherein the covering layer has a thickness that is a multiple of ¼ of wavelength of ultrasonic waves transmitted from the unimorph-type ultrasound probe.

19. A method for manufacturing a unimorph-type ultrasound probe, comprising the steps of:
forming a plurality of piezoelectric element regions in a substrate;
forming a plurality of openings, each of which has a predetermined shape, in each of the plurality of piezoelectric element regions on the substrate and forming a plurality of vibration plates, each of which closes one end of the plurality of openings in each of the plurality of piezoelectric element regions, on the substrate;
forming a plurality of piezoelectric element portions in each of the plurality of piezoelectric element regions on a surface of the plurality of vibration plates, the plurality of piezoelectric element portions having a plurality of piezoelectric substance layers, a plurality of first electrode layers disposed on one surfaces of the plurality of piezoelectric substance layers, and a plurality of second electrode layers disposed on the other surfaces of the plurality of piezoelectric substance layers;
forming a plurality of lead-out electrodes disposed on a surface of the substrate corresponding to the plurality of piezoelectric element regions;
uniting the plurality of first electrode layers of the plurality of piezoelectric element portions formed in each of the plurality of piezoelectric element regions as one by connecting to each other and connecting the plurality of first electrode layers to a corresponding lead-out electrode; and
forming a covering layer, which is formed of an organic resin having an acoustic impedance of $1.5 \times 10^6$ kg/m² s to $4 \times 10^6$ kg/m² s and has a Shore A hardness of equal to or less than 75, on the surface of the substrate such that the plurality of piezoelectric element portions in each of the plurality of piezoelectric element regions are buried under the covering layer.

* * * * *